United States Patent [19]

van Arragon et al.

[11] Patent Number: 4,513,743
[45] Date of Patent: Apr. 30, 1985

[54] PHYSIOLOGICAL DEVICES SUCH AS PACEMAKERS AND METHOD FOR PROVIDING HISTOGRAM DATA

[75] Inventors: Gerrit W. van Arragon, Dieren; Kornelis A. Mensink; Frederik H. M. Wittkampf, both of Brummen, all of Netherlands

[73] Assignee: Vitatron Medical B.V., Netherlands

[21] Appl. No.: 441,053

[22] Filed: Nov. 12, 1982

[51] Int. Cl.³ .............................................. A61B 5/00
[52] U.S. Cl. ............................................. 128/419 PG
[58] Field of Search ................................ 128/695–712, 128/419 PT, 419 PG, 903–904; 364/565, 554

[56] References Cited

U.S. PATENT DOCUMENTS

| | | | |
|---|---|---|---|
| 3,554,187 | 1/1971 | Glassner et al. | 128/706 |
| 3,658,055 | 4/1972 | Abe et al. | 128/703 |
| 3,820,025 | 6/1974 | Lahr et al. | 128/708 |
| 3,880,147 | 4/1975 | Gruenke et al. | 128/702 |
| 3,911,905 | 10/1975 | Rossel | 128/709 |
| 3,946,744 | 3/1976 | Auerbach | 128/419 PT |
| 3,991,748 | 11/1976 | Ohlsson | 128/709 |
| 4,232,679 | 11/1980 | Schulman | 128/419 PG |
| 4,340,065 | 7/1982 | Gessman | 128/712 |
| 4,355,365 | 10/1982 | McCracken et al. | 364/569 |
| 4,364,397 | 12/1982 | Citron et al. | 128/710 |
| 4,387,717 | 6/1983 | Brownlee et al. | 128/419 PG |
| 4,393,874 | 7/1983 | Nappholz et al. | 128/697 |

FOREIGN PATENT DOCUMENTS 721079   3/1980   U.S.S.R. ............................... 128/703

Primary Examiner—William E. Kamm
Assistant Examiner—Mitchell J. Shein
Attorney, Agent, or Firm—Woodcock Washburn Kurtz Mackiewicz & Norris

[57] ABSTRACT

A physiological device adapted for implantation in a human patient, e.g. a cardiac pacemaker or muscle stimulator, characterized by having programmable means for generating data and assembling same for presentation of one or more histograms. The implanted device has circuitry for registering the occurrence of sensed or evoked events, as well as device operating events such as cycles of operation, and means, preferably software control of a microprocessor, for classifying registered events into respective classes of one or more parameters associated with the events and for accumulating counts of events for each such class. The system also includes external apparatus for communicating programmed instructions to the device, whereby histogram selection and histogram classes are programmed, and for receiving the histogram data transmitted from the implanted device and displaying it in a convenient histogram form. Time based histograms are also generated, utilizing a software clock for continuously tracking time.

34 Claims, 9 Drawing Figures

PHYSIOLOGICAL DEVICES SUCH AS PACEMAKERS AND METHOD FOR PROVIDING HISTOGRAM DATA

BACKGROUND OF THE INVENTION

This invention relates to physiological devices such as pacemakers, muscle stimulators and the like and, in particular, implantable devices having means for sensing given natural events in the patient or events produced by the device, and having means for obtaining and delivering histogram data concerning such events.

Pacemaker design has evolved very rapidly over the last several years. There has been a great advance in the area of programmability of pacemakers, to enable them to be programmed to control pacemaker operation, to work with different selectable operation parameters, and to work in different fundamental modes. Likewise, other physiological devices such as muscle stimulators, artificial drug injectors and the like have undergone substantial advances. In the area of programmable pacemakers, microprocessors are now utilized as a central means for providing flexible programming and control of the pacemaker operation. See, for example, European Patent Application 81108940.8, assigned to the same assignee, which is incorporated herein by reference. As disclosed there, the microprocessor can be incorporated into a pacemaker design for carrying out desired control subroutines, interrupts, and receipt and use of program data transmitted from a location external to the implanted pacemaker. Further, the speed and increased flexibility of microprocessor control enables cycle to cycle adjustments, permitting pacer design to optimize one or more selected parameters, such as pacer rate and escape interval, in view of sensed cardiac conditions.

While adaptive pacemaker control has been accomplished to a great degree in the pacemaker field, as disclosed in the above referenced EPO patent specification, relatively little development has taken place in the area of providing diagnostic information to the physician or user of the device, particularly in the case of implanted devices. One reason for this has been the prior limitation on the ability of an implanted device to accumulate and store sufficient quantities of data to provide meaningful information. For example, in the pacemaker area, systems have been developed which are able to transmit to the physician information about the current pacer operation, including such parameters as pacing rate, stimulus pulse level, refractory interval, etc. However, very little has been done in accumulating and making available device-patient data over any extended period of time, which the physician can use for diagnostic purposes. It is evident that if the physician were to have available a more complete history of the device operation and the patient response thereto, more intelligent judgment could be reached concerning the programming of the on-going device operation. Accordingly, there remains a substantial need, which this invention meets, for an implanted physiological device with means for recording events and parameters related thereto, and assembling data representative of such recorded information in such a way that it can be efficiently transmitted for external display and use.

SUMMARY OF THE INVENTION

It is an object of this invention to provide an implantable physiological device, such as a pacemaker or muscle stimulator having improved means for registering and storing event data related to the operation of the device, and arranging such storage data in histogram form, whereby histograms can be made available to the user.

It is another object of this invention to provide an improved physiological stimulating device having means for compiling diagnostic data relating to patient and device events, and making such data available in histogram form.

It is another object of this invention to provide a pacemaker system, including an implantable pacemaker, an external programmer device and external data input-output apparatus, having the capacity for generating and displaying diagnostic data in histogram form, and further having the capacity for external programming of histogram limits used in the implantable pacemaker.

It is another object of this invention to provide a diagnostic physiological device, adapted to deliver simulus signals to a patient, to sense the occurrence of events in a patient, or both, and to provide time-based histogram data in either continuous or alternating histogram form.

It is another object of this invention to provide a system having an implantable cardiac pacemaker and means for programming said pacemaker to compile histogram data, including histograms which alternate with registered events or histograms which alternate with time, or both.

It is another object of this invention to provide an implantable microprocessor controlled physiological device having a software controlled timing means, or clock, for continuously tracking time, whereby time of events can be stored and transmitted for external recording, and time based histogram data can be generated.

It is another object of this invention to provide a method of generating diagnostic histogram data in an implanted physiological device, including generating histograms characterized by parameter classes and/or time classes.

DESCRIPTION OF THE PREFERRED EMBODIMENT

DESCRIPTION OF BASIC HARDWARE AND SOFTWARE

In the description of the preferred embodiment, a cardiac pacemaker is used as the illustrative embodiment. However, it is to be understood that the invention applies equally to other types of devices adapted to interface with a patient, and to deliver electrical signals and/or sense electrical activity or other events in the patient.

Figure 1:
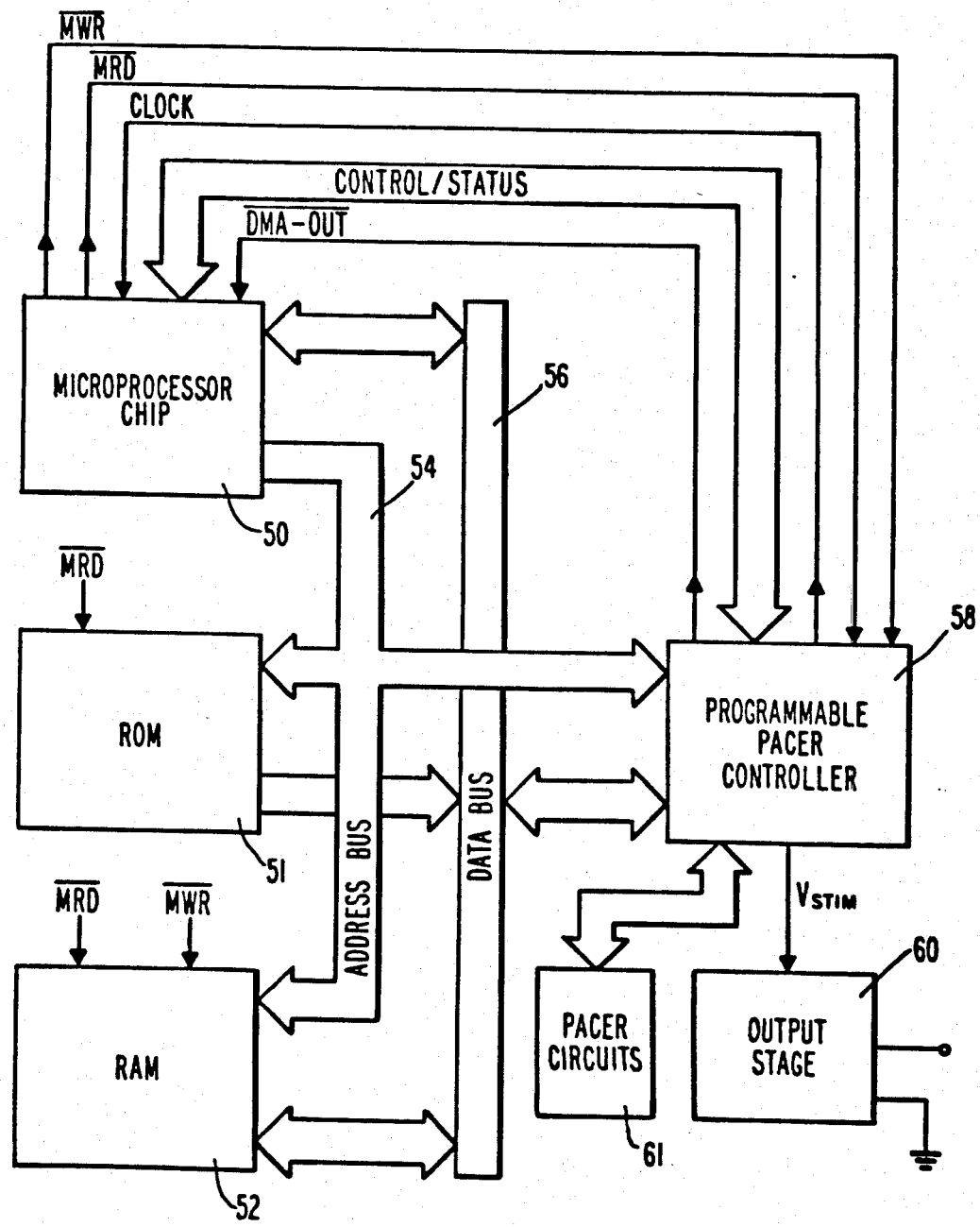
FIG. 1 is a block diagram of the basic hardware components of a pacemaker embodiment of the invention.

Referring now to FIG. 1, there is shown a block diagram of the primary hardware components of the apparatus of this invention. Shown in block 50 is a microprocessor chip, and as used hereinafter, the term microprocessor or microprocessor element means a commercially available microprocessor, whether of one or more chips. The term "microprocessor", as used in defining this invention, can embrace any equivalent computing device or system. A preferred microprocessor for use in the application of this invention as part of a programmable cardiac pacer is the CDP 1802 microprocessor made by RCA. The CDP 1802, hereinafter the 1802, is fabricated on a single chip utilizing a silicon gate CMOS structure. Because of its CMOS structure, it offers the design advantages of wide operating temperature range, relatively high speed, high noise immunity an in particular, low power consumption. It is to be understood that particularly for an implantable device application, where the lifetime of the battery source is important, the low power CMOS microprocessor is particularly advantageous. Another suitable microprocessor is the Hitachi 6301.

Descriptions and specifications of the CDP 1802 are freely available and in the technical literature, and accordingly, a full description of the microprocessor is not necessary in this specification. However, some further comments are useful for clarifying the description of this invention. The CDP 1802 has a 40 pin circuit. A standard bidirectional parallel data bus 56 utilizes 8 pins, BUS0–BUS7. All parallel data communications between the CPU and external logic, memory or I/O occur via this data bus. There is an 8 bit address bus, represented by the numeral 54. All addresses must be multiplexed; the high order address byte is first outputted, followed by the low order address byte. It is to be noted that compatible memory is used with the CDP 1802 which includes address decode logic. There are 7 status flag pins, including Data Flag and Interrupt Enable Flag, 4 I/O flags and a Q Status Flag which can be set or reset directly by appropriate instructions. There are 4 timing signals, namely CLOCK, $\overline{XTAL}$, $\overline{TPA}$ and $\overline{TPB}$. CLOCK is the principle timing signal input from an external clock which in this invention is mounted on programmable pacer controller 58 and controlled by logic within that controller. The frequency of the clock may be up to 6.4 MHz, but for this application is 40 KHz. When using the on-chip clock logic of the microprocessor, an external crystal must be connected with a parallel resistor to the $\overline{XTAL}$ and clock pins. $\overline{TPA}$ and $\overline{TPB}$ are timing pulses output by the microprocessor each machine cycle, to control external logic. The remaining pins are control pins, including $\overline{MWR}$ and $\overline{MRD}$ which control memory operation, and the DMA pins which control direct memory access operation.

Still referring to FIG. 1, the address bus 54 is shown interconnected with ROM memory 51, RAM memory 52, and the programmable pacer controller circuit 58. The ROM is suitably an RCA model CPD 1833 while the RAM is suitably an RCA model CDP 1822 chip. The data bus 56 interconnects the microprocessor chip 50 with ROM 51, RAM 52 and pacer controller 58. Reference is made to copending EPO application Ser. No. 108,939 (DEA-20714) which describes additional detail of controller block 58, and which is incorporated by reference. Although only one ROM and one RAM block are shown, it is to be understood that there is no limitation on the amount of memory subject only to practical design considerations. As further shown in FIG. 1, the output of controller block 58, which is a timing signal represented as $V_{stim}$, is connected to a conventional output stage 60 for developing an output signal to be delivered to a patient's heart. It is to be understood that for a pacer application other circuitry is incorporated, including timing logic for determining the rate and circumstances for delivering output pulses; an input path for receiving natural heart signals and amplifying same, receiving means for receiving external program signals and modifying operating parameters in accordance with such external signals; etc. All these functions are conventional and well described in the patent literature, and are carried out either in controller block 58 or in circuitry represented by block 61 which is shown communicating with controller 58. The pacemaker may be a single chamber or dual chamber (AV) device, and operate in any of the known pacemaker modes. Means for communicating with external apparatus, as discussed in connection with FIG. 6, may be incorporated into block 58 and/or block 61.

Figure 2A:
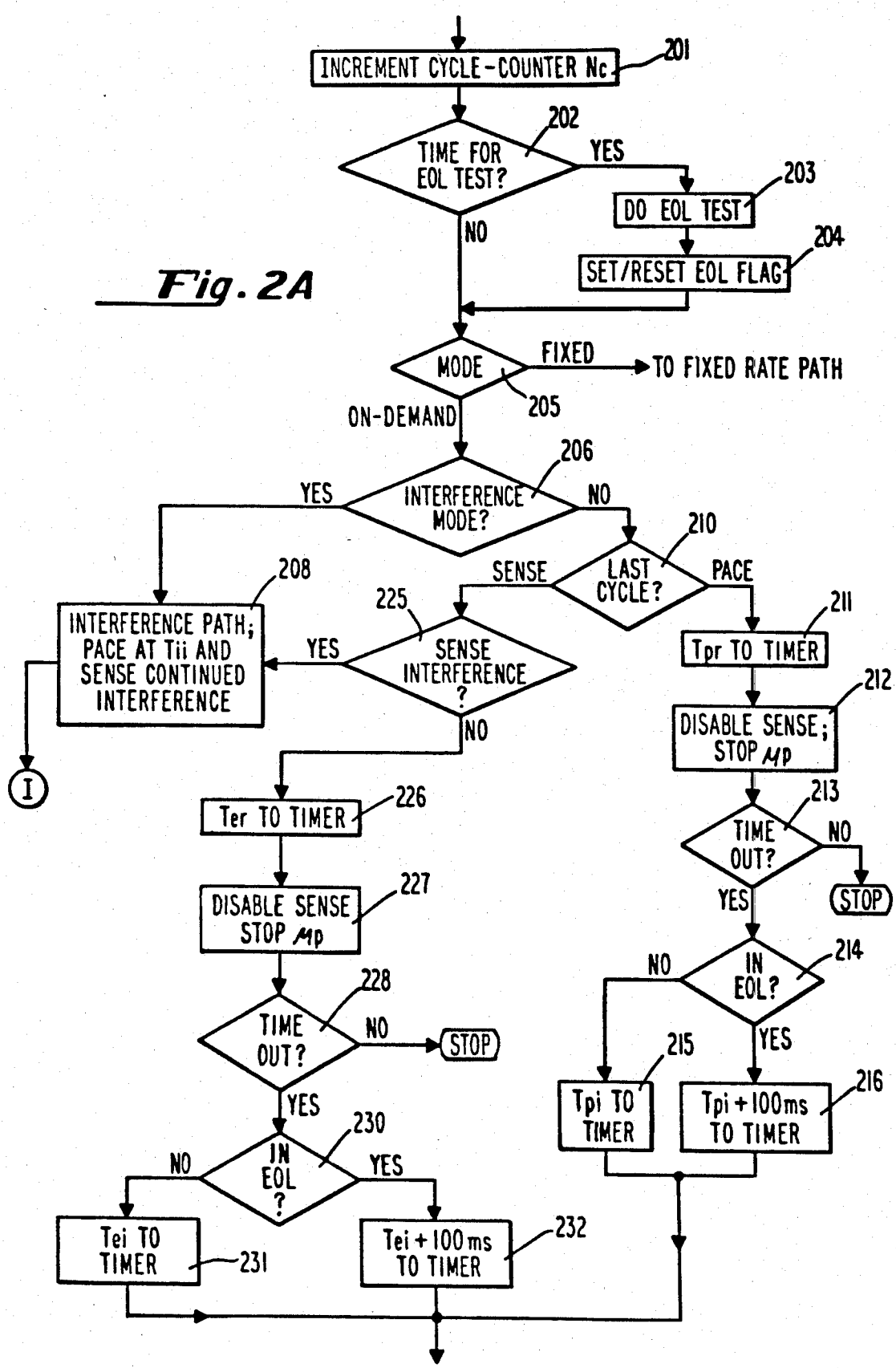
FIGS. 2A and 2B constitute a flow diagram of a simplified routine suitable for use with a pacemaker in accordance with this invention, and illustrating program control of certain functional steps carried out each pacer cycle.
Figure 2B:
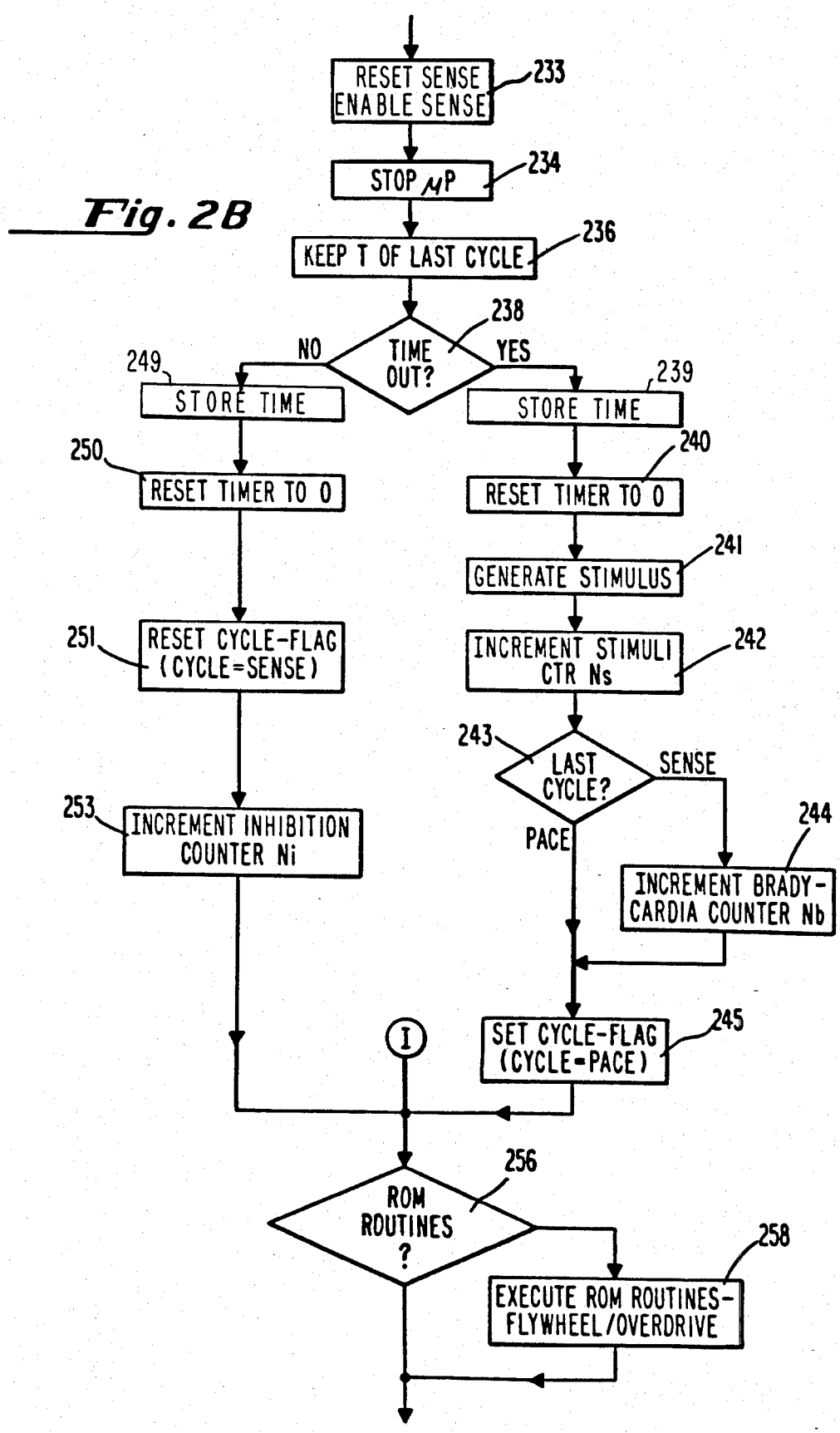

Referring now to FIGS. 2A and 2B, there is shown an illustrative flow diagram of a program routine which is run once each cycle in the pacer of this invention. This routine does not contain all steps which are carried out by the microprocessor, but contains steps which are illustrative of the operations which relate to the subject invention. Although illustrated for a single chamber pacer, either atrial or ventricular, the flow diagram is also illustrative of programmed operations carried out in a dual chamber pacer or other device using this invention.

FIGS. 2A and 2B together comprise a portion of the flow diagram of an overall cycle routine which is run by the microprocessor every pace cycle. The program is stored in ROM, but many of the variables of the software-controlled operations can be re-programmed through the RAM memory. Optional subroutines may be stored in RAM.

Starting at block 201, the cycle counter is incremented, thereby providing a running count $N_c$ of the number of cycles. In the discussion of histograms that follows, an increment cycle, or pacer interval, is an example of an "event" that is classified according to predetermined limits of a given parameter, or as a function of time. At block 202, the program determines whether it is time to run an end of life (EOL) test, i.e., the test is run once after passage of a predetermined number of cycles. If the answer is yes, the test is performed at block 203, and the EOL flag is set or reset at block 204 in accordance with the test result. The test is carried out by measuring the battery voltage and comparing it to a reference, the details of the test being not pertinent to this invention. Following this, at block 205, it is determined whether the pacer is in a "fixed" rate mode or is operating "on-demand". If it is in fixed rate mode, the program branches to a separate fixed rate path which is not shown. The following portion of the flow diagram illustrates the primary components of the on-demand path.

At block 206, the program determines whether the pacer is in an interference mode, by checking data generated during the last cycle. If it is found that the pacer is in the interference mode, the path branches through block 208, designated Interference Path. The details of this path are not included, but basically this path senses whether interference has continued, and causes the pacer to pace at a special programmed rate having an interval $T_{ii}$. At the end of the interference path the program branches, as shown at the output I, to the bottom of the cycle routine as seen at the bottom of FIG. 2B.

If the pacer is not in the interference mode, a determination is made at block 210 as to whether the last cycle ended with a pace pulse or a sensed heartbeat. For a pace pulse, the right hand branch is taken. At block 211 the timer which was reset to zero near the end of the last cycle is set to time out after an internal $T_{pr}$ the pacing refractory interval. For purposes of the flow diagram, it is assumed that timing operations are carried out by conventional circuitry external to the microprocessor, utilizing circuitry on the controller chip 58 which is in communication with the microprocessor chip 50. Following setting the time out interval, at block 212 the microprocessor generates a signal which is outputted through controller 58 to disable the sensing circuitry, and to cause the microprocessor to be stopped. During the time that the microprocessor is stopped, clock signals from controller 58 are not transmitted to the microprocessor chip 50, thereby saving the power that would otherwise be required to operate the microprocessor.

In normal operation, the microprocessor is started again when the timer times out due to elapse of the interval $T_{pr}$ causing clock pulses to be gated to the microprocessor, thereby starting its operation again. At block 213, it is determined whether the microprocessor was started by a time out of the timer, which would be determined by checking an appropriate status signal inputted from controller 58 to the chip 50. Assuming a proper time out, meaning that the refractory interval has ended, the program goes to block 214 and determines if pacer operation is in the EOL mode, by checking the EOL flag as determined at block 204. Assuming no EOL operation, at block 215 the programmed pacing interval time $T_{pi}$ is transferred from the microprocessor to the timer, so that another output signal is generated by the timer when it reaches the value $T_{pi}$. Note that at this point the timer is not reset, but rather the controller circuit is programmed to produce another signal when the time reaches the value $T_{pi}$. If the pacer is in EOL mode, the program branches to block 216 where the pacing interval is set at the programmed $T_{pi}$ value plus 100 ms, thereby causing a reduced rate of operation during EOL conditions. This technique results in reduced power drain after EOL has been detected, due to the lower rate of producing pacing pulses.

Returning to block 210, if the last cycle was determined to have terminated with a sensed heartbeat, the program proceeds to the left path. At block 225, a series of instructions are carried out over a period of time which is less then the refractory interval, to determine whether interference is still present. If the answer is yes, the program branches to block 208 to continue the cycle. Assuming no interference, the program proceeds to block 226, where the timer is loaded with $T_{er}$ the escape refractory interval. Following this, at block 227, the sense circuitry is disabled, since the pacer is within the refractory interval, and the microprocessor is stopped and stays stopped until started again by a signal from controller 58. When started again, the program determines, at block 228, whether there has been a time out of the escape refractory interval. Assuming so, at block 230 the program checks to see if the pacer is in the EOL mode. If not, the program value of the escape interval $T_{ei}$ is sent to controller 58 at block 231, to cause a timer output when it times out such interval. If the pacer is in EOL, the escape interval is enlarged by 100 ms, as shown in 232.

Continuing the program flow chart, as seen in FIG. 2B, the pacer resets and then enables the sense circuitry, as designated at block 233. This is done since the refractory interval has now been timed out, and the pacer is to be enabled so as to sense a natural heartbeat. Following this, the microprocessor is stopped at 234, by sending a status signal to controller 58 which causes opening of the return path which connects clock signals to the microprocessor chip 50. While the microprocessor is thus off, the timer is timing out the escape interval. During this time, a received natural beat will be processed by controller 58 to generate a status signal and restart the microprocessor, and likewise a time out of the timer will again start the microprocessor. When the microprocessor starts again, the time T of the last pacer cycle is read from the timer and stored, as shown at 236. The interval time T, which is inversely related to rate, is a parameter which may be used for generating a histogram such as shown in (a), (b) or (e) of FIG. 3. At block 238, a determination is made as to whether there has been a time out, by checking the status signals from controller 58. If yes, a stimulus pulse is to be delivered and the program takes the right hand path. If no, logic indicates that a spontaneous heartbeat has been received and the program takes the left hand path.

Assuming a time out, the time T is cumulatively added, at block 239, to provide a continuously running software "clock". Alternately, the time can be accumulated as part of the operation at block 236. The timer is then reset to zero at block 240, and at block 241 the program causes transmission of the necessary information to controller 58 to cause generation of an output stimulus pulse, or a series of pulses. This is suitably done by utilizing the DMA mode of the microprocessor, as described in co-pending EPO application No. 81108939.0. At block 242, a stimulus counter is incremented, to keep a running total of delivered stimuli, $N_s$. At block 243, the program recalls whether the last prior cycle had ended with a sense or a pace by checking the cycle-flag. If the answer is sense, this means there has been a transition to pace due to the absence of a natural pulse during the escape interval, and at block 244 a bradycardia counter is incremented to keep a running total $N_b$ of such events. A bradycardia flag may be set, to indicate the presence of a bradycardia "event" for histogram purposes. Following this, at block 245 the program sets the cycle flag to indicate that the last cycle terminated in a delivered paces pulse. This flag also registers the occurrence of a delivered stimulus event.

Returning to block 238 and taking the left hand path, corresponding to a received QRS, the continuous software clock is incremented by adding the time T of the last cycle. Note that whichever way the program branches at 238, the total time is incremented by T. The time taken to carry out the intervening instructions of step 238, which is predetermined and thus known, can be added by the program. Of course, the time increment can be added immediately following step 236, which reduces the number of intervening instructions. The timer is reset to zero at block 250 and at block 251 the cycle flag is reset to indicate that the cycle terminated with a sensed heartbeat. This also registers the occurrence of a sensed natural heartbeat event. At block 253, an inhibition counter is incremented to keep a tally $N_i$ of such inhibition events.

At the bottom of FIG. 2B, the three above described paths are joined, together with the fixed rate path which is not illustrated, and it is determined whether the pacer is programmed to carry out additional routines stored in ROM 51. If yes, the program branches through block 258 to execute those ROM routines, which include the histogram routines illustrated in FIGS. 5A and 5B. These routines could likewise be stored in RAM 52.

The above flow chart description has made frequent references to setting and resetting the timer, determining when the timer has reached a set value, and starting and stopping the microprocessor. Such operations may be carried out entirely by software, or software-controlled hardware. For the preferred embodiment of this invention, the control circuitry for carrying out these functions is located on a chip which houses controller 58 and which, as seen in FIG. 1, is interconnected with the microprocessor and memory by the address bus 54, data bus 56 and control lines which are connected to microprocessor chip 50. The pertinent details of the programmable pacer controller (PPD) are discussed in EPO application No. 81108940.8, assigned to the same assignee, which is incorporated by reference.

DISCUSSION OF HISTOGRAMS AS USED IN THIS INVENTION

The histogram, as used in the apparatus and method of this invention, comprises a compilation of the occurrences of events distributed by some parameter in a compressed form. The period of registering and compilling the occurrence of events can be continuous, i.e. the entire lifetime of a cardiac pacemaker, or can be limited to a predetermined time, such as 10 minutes, one hour, one day, etc. The histogram is essentially a technique for compilling and presenting information in a compressed form, so as to give a profile of a given event or events as a function of a predetermined associated parameter. For the example of a cardiac pacemaker, sensed events include QRS waves, P waves, PVCs (premature ventricular contractions) and PACs (premature atrial contractions). Examples of delivered events are the ventricular stimulus and the atrial stimulus. The number of pacer intervals is an event which, for a demand type pacer, includes both sensed and delivered events. Examples of parameters include the pacer rate, or interval; V-PVC interval; peak QRS amplitude; A-V interval; A-A interval; peak P amplitude; and stimulus amplitude, width or interval.

In histograms for the pacer embodiment, three modes of distribution can be defined. First, the events can be distributed over classes based on the parameter of the event itself. Refering to FIG. 3(a), the number of intervals is plotted on the Y axis for events, and the parameter classes are plotted on the X axis. As shown, the parameter is atrial rate, which is a parameter of each interval, and thus of the event itself. As shown, the histogram has ten classes, the classes being adjacent and each being defined by an upper limit. The table below presents typical programmed class limits, for 8 classes:

Class 1-rate between 0 and 50 ppm (LN=1)
Class 2-rate between 51 and 60 ppm (LN=2)
Class 3-rate between 61 and 70 ppm (LN=3)
Class 4-rate between 71 and 81 ppm (LN=4)
Class 5-rate between 81 and 90 ppm (LN=5)
Class 6-rate between 91 and 100 ppm (LN=6)
Class 7-rate between 101 and 120 ppm (LN=7)
Class 8-rate between 120 and 250 ppm (LN=8)

Figure 3:
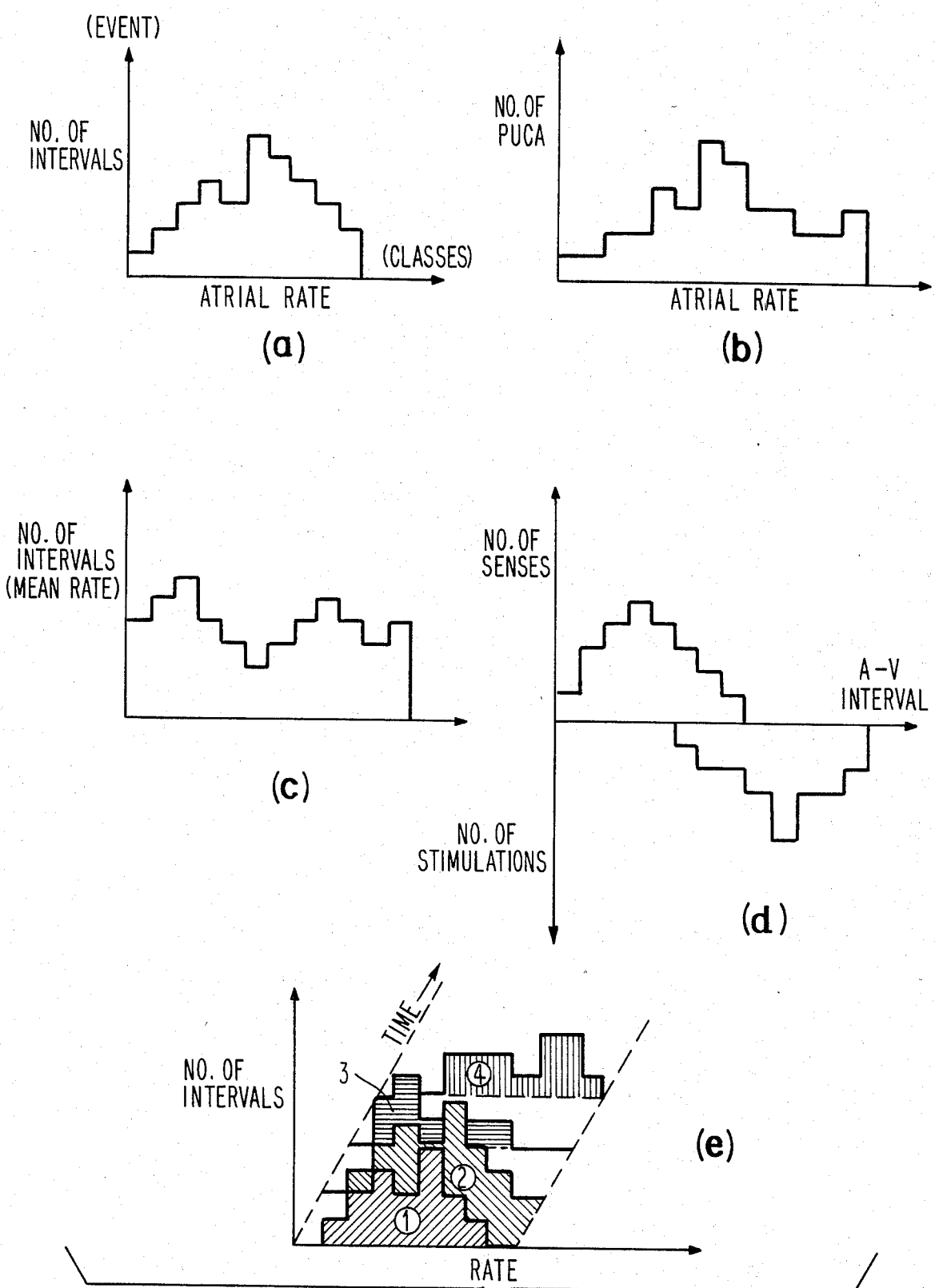
FIG. 3 is a series of graphs illustrating different types of histograms made available by the apparatus and method of this invention.

The table above is illustrative, it being understood that the limits of the classes can be programmed as desired by the user. Also, the number of classes utilized is a matter of choice, it being noted that the table shows eight classes while the histograms of FIG. 3 show different numbers of classes.

A second mode of distribution is where the events are distributed over classes based upon a parameter occurring simultaneously with the event, as illustrated in FIG. 3(b) where the number of PVCs are distributed over classes set by the length of the A-A interval, or the atrial rate.

Referring now to FIG. 3(c), there is shown a histogram where the occurrence of events (intervals) is distributed by classes which represent ranges of the time of day. As shown, the classes are broken into 12 two hour intervals, such that the histogram gives a relative indication of the number of intervals or mean rate, for each two hour time interval of the 24 hour day. This enables the doctor to get a measure of the variation of the patient's rate as a function of his daily activity.

Referring to FIG. 3(d), there is shown an example of compiling two histograms in parallel. For the example given, the number of sensed heartbeats is plotted against the AV interval, and the number of stimulated heartbeats is likewise plotted against the AV interval. FIG. 3(e) gives an example of plotting histograms in series, or time sequence. As illustrated, 4 histograms are plotted, providing an illustration of changes in rate distribution with time. An additional histogram, within this invention, comprises a three dimensional histogram, for example, wherein the events are pacer intervals; classes of atrial rate are plotted on the X-axis; and AV time distribution is plotted on the Y-axis.

Figure 4:
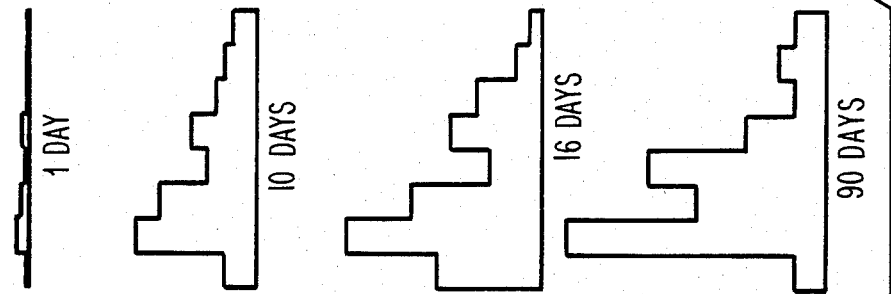
FIG. 4 is a series of diagrams illustrating an alternating histogram and a continuous histogram in accordance with this invention.

Referring now to FIG. 4, there are illustrated histogram sequences which show the difference between a continuous histogram and an alternating histogram, as utilized in this invention. In FIG. 4, the events and parameters are not identified, but any of the above-mentioned events and parameters can be assumed. The purpose of FIG. 4 is to illustrate the difference between compiling a continuous histogram wherein the number of events is continuously accumulated for each class, with the alternating histogram where the events per class are accumulated for a given length of time, whereafter that histogram is held constant in storage and a new histogram is generated over the same length of time. As illustrated, parameters are divided into 8 classes, and the storage cycle length is defined as 7 days. In other words, a first histogram is built up for 7 days, whereupon it is classified as "previous" and held, for operator observation, during the next 7 day cycle while the then current histogram is developed. After the second 7 day cycle has been run, the first histogram is erased from memory, the second one is held in storage, and a third one is generated. Thus, the device always has a histogram available for the previous cycle, and a current histogram for the current cycle. Although two alternating histograms are illustrated, it is clearly within the scope of the invention to provide n histograms, where n is any number of histograms that might be desired to be stored. The example illustrated in FIG. 3(e) is an alternating histogram where four histogram cycles have been stored, and displayed together. Likewise, the storage cycle length may be any period of time, such as one day, one week, one month, one year, etc. The mode of histogram generation, i.e. continuous or alternating, the choice of storage cycle length, and the events and parameters utilized for the histogram or histograms, are operator selectable. Means for presenting the histogram data, e.g., on a video terminal, are state of the art.

DESCRIPTION OF HISTOGRAM AND TIME-BASED DATA GENERATION

Figure 5A:
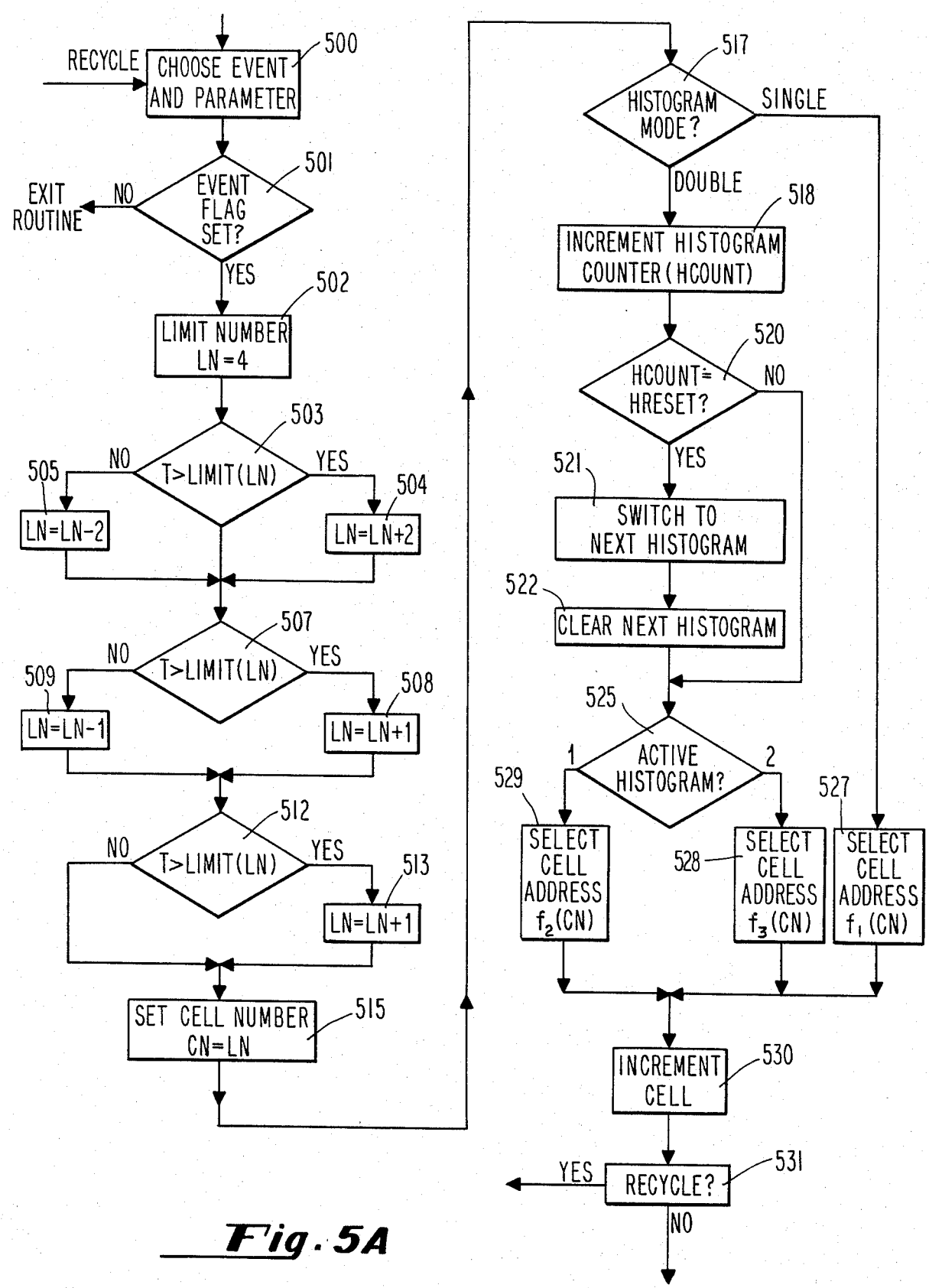
FIG. 5A is a flow diagram showing the steps taken in classifying an event in terms of a specified associated parameter.

Referring now to FIG. 5A, there is shown a block diagram illustrating a microprocessor subroutine for classifying a registered event, and thus building up a histogram. In the example as illustrated, the parameter is T, or pacer interval, which is a measure of rate. Other parameters can be used instead of T, including the time of day. The event could be any one of the above enumerated events, the occurrence of which is known by the microprocessor due so the setting of an appropriate flag. If the event to be classified is increment or pacer cycle, as counted at block 201, there is no need to set a flag since the subroutine is only run once each pacer cycle. The subroutine is conveniently one of the ROM routines, which is selected at block 256 as shown in FIG. 2B. By way of further example, if the desired event for the histogram is a sensed QRS signal, note that the sense flag has been set at block 251; if the desired event is a delivered stimulus signal, the desired flag has been set at block 245. In a like manner, respective other flags have been set or reset, to indicate the occurrence of the event which is to be plotted in the histogram.

Referring specifically to the flow diagram of FIG. 5A, the event and parameter for the histogram being developed is chosen at block 500. If the device is programmed to compute a continuous, i.e. single histogram, there is of course no need to make a choice. However, if alternating or plural histograms are being generated, then it is necessary to serially classify each event in terms of its associated parameter. At block 500, it is determined whether or not an event flag, for the chosen event, has been set. For example, if the event is PVC, most frequently the event will not have occurred, and the subroutine simply exits. However, assuming the event has occurred, the routine proceeds to block 501 where the limit number LN is set equal to 4, as a means of initiating the search to determine the parameter classification for the event that has just occurred. At 502, the parameter is compared with the limit corresponding to limit number 4. By way of the example of rates as given hereinabove, limit 4 corresponds to 81 ppm (which in turn corresponds to a given interval T). If T is found to be greater than the upper limit of the fourth class, the program switches to block 504, where LN is set equal to LN+2, corresponding to the sixth class limit. If T is found to be less than the fourth class limit, the program switches to block 505, and sets LN equal to LN−2, corresponding to the second class limit. At 507, there is again a determination of whether T, or the chosen parameter, is greater than the limit corresponding to the class set by LN. If the answer is yes, the routine branches to block 508, where LN is incremented again by 1. If the answer is no, the routine branches through block 509, where LN is decremented by 1. At 512, the comparison between T and the limit for the class corresponding to LN is again made. If T is greater than the limit, LN is incremented by 1 at block 513. If T is less than the limit corresponding to LN as then set, the routine branches directly to block 515. It can be seen that in stepping from 501 through to 515, the program has determined whether the parameter associated with the event that is being counted falls within class 1, 2, 3, 4, 5, 6, 7, or 8. Of course, other logical arrangements can be devised for making this determination, and the example of 8 classes is illustrative only.

At block 515, a cell number CN is set equal to LN. It is then determined whether the histogram mode is single or double, at 517. If single, the routine branches directly to 527, where a cell address is selected, which is a first function of CN, $f_1(CN)$. Thus, at 527, the program selects a given cell from a group of eight cells which is being used for the single, or continuous histogram, corresponding to the determined class. At block 530, the contents of the cell at the selected cell address is incremented by 1. Going back to the choice at 517, if the histogram mode is double, meaning that an alternating histogram is being generated, the histogram counter is incremented at block 518. At 520, it is determined whether the histogram count HCOUNT is equal to the limit set for alternating, HRESET. It is to be understood that in this mode the histogram alternates as a function of counted events, and the decision at 520 is made each program cycle to determine whether the histogram should be alternated. If the answer at 520 is no, the routine skips directly to 525. If the answer is yes, the program switches to the next histogram at block 521, which is cleared at 522 to be able to start over again. At 525, it is determined which histogram is active, i.e. one or two, it being understood that the other histogram then remains inactive. Depending upon the decision at 525, a cell address is selected at 528 or 529 as a function of cell number CN. The first alternating histogram is maintained in 8 address locations, and the second histograms is maintained in another 8 address locations. Having selected the proper cell address, the contents of the cell found at that address are incremented at block 530. Then, at block 531, it is determined whether the program should recycle back to block 500, to generate another histogram.

Figures 5B, 5C:
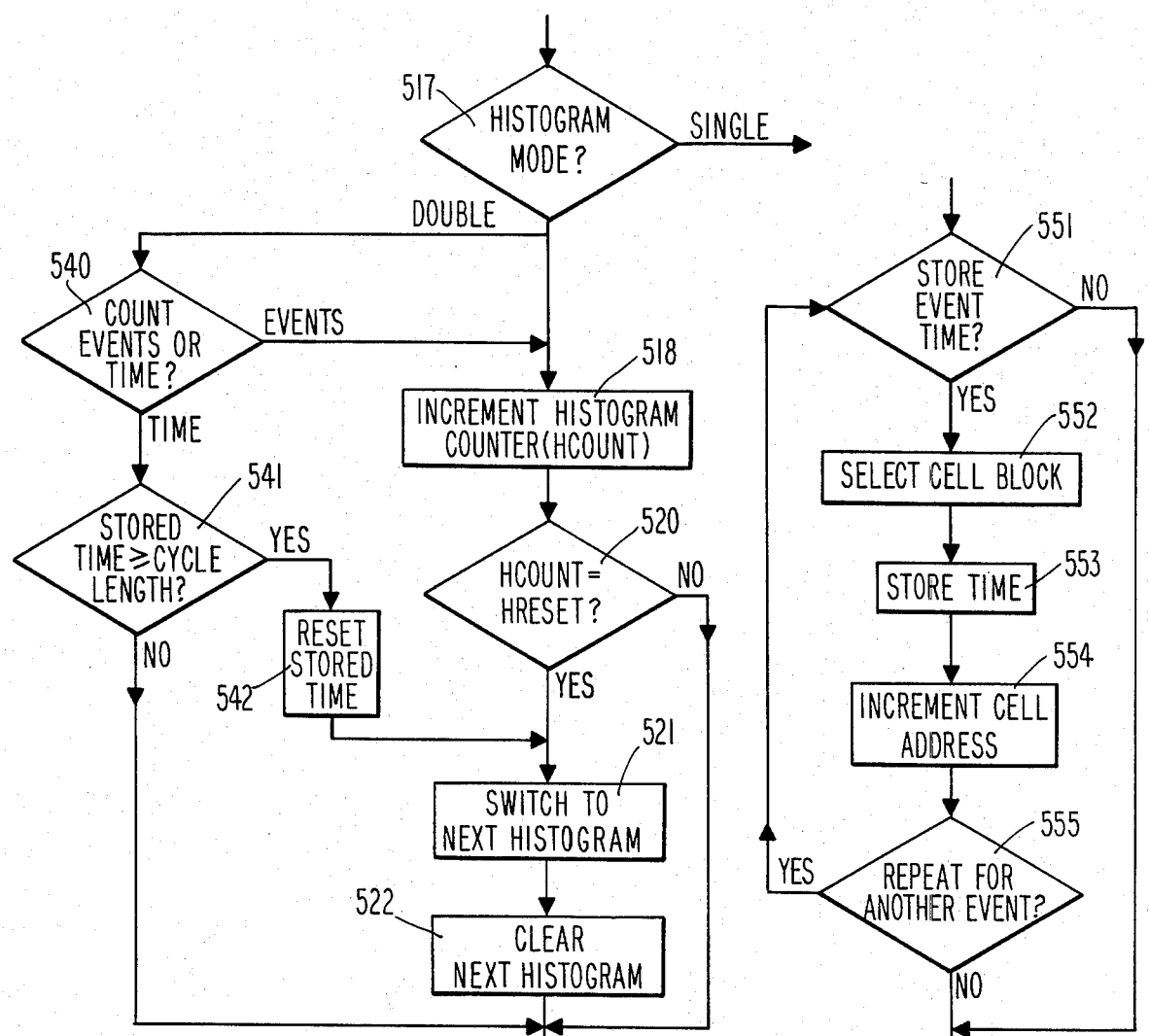
FIG. 5B is an alternate flow diagram for classifying an event in terms of time or in terms of a given associated parameter.
FIG. 5C is a short flow diagram for storing the actual time of any given event.

Referring now to FIG. 5B, there is shown a modified portion of the flow diagram of FIG. 5A, to provide for alternating histograms of the nature shown in FIG. 4, i.e. alternating as a function of time. At 517, it is determined whether or not the histogram is in the double mode. If so, the program branches to 540, where it is determined whether the device is programmed to count events or time. In other words, at this point the device determines whether the alternating of the histogram is based upon the passage of a predetermined number of events, or upon the passage of a certain amount of time. If the histogram is to alternate as a function of counted events, it branches to 518 and proceeds as discussed above in relation to FIG. 5A. If the histogram is to alternate as a function of time, the program proceeds to 541, where the stored time, from block 239 or 249 as seen in FIG. 2B, is compared to the programmed cycle length. If the stored time has become equal to or greater than the cycle length, then the program transfers to block 521, where it then switches to the next histogram. If the stored time has not reached the cycle length, then the program skips blocks 521 and 522, and proceeds on to block 525 as shown in FIG. 5A. Thus, the device can be programmed to alternate either as a function of counted events or of time.

Referring now to FIG. 5C, there is shown a short flow diagram for storing the actual time of any given event. This can be useful in informing the doctor as to exactly when certain events, such as DVCs or PACs, occurred. It is to be kept in mind that the stored time is available continuously, and any pacer cycle when an unusual event such as a PVC or PAC occurs, the actual time can be stored in memory. The times for each such event can be read out any time later by the doctor, thus obtaining a precise history of such events. Normally this is to be done only with events that occur relatively infrequently, and even so it may be desirable to limit the number of such events which are stored so that, for example, only the last 10 such events are kept in storage. At 551, it is determined whether the device has been instructed to store the time of occurrence of an event. If yes, at block 552 the program selects a cell block, e.g. 10 address locations corresponding to the event that is being monitored. For example, if 5 events are being monitored, 5 different blocks of 10 memory locations each may be assigned for storing event times. At 553, the time of occurrence of an event is actually stored at a memory location corresponding to a given cell address. At block 554, the cell address is incremented so that the next event occurrence will be stored in a successive cell location. At the same time, although not shown in FIG. 5C, the microprocessor checks to see if the cell address has been incremented past the last, e.g. tenth, address location for the block, in which case the cell address counter is reset to the first address location. At block 555, it is determined whether the device is programmed to store the time of any other event which may have occurred during the same cycle, in which case the subroutines branches back to 551 and repeats.

Figure 6:
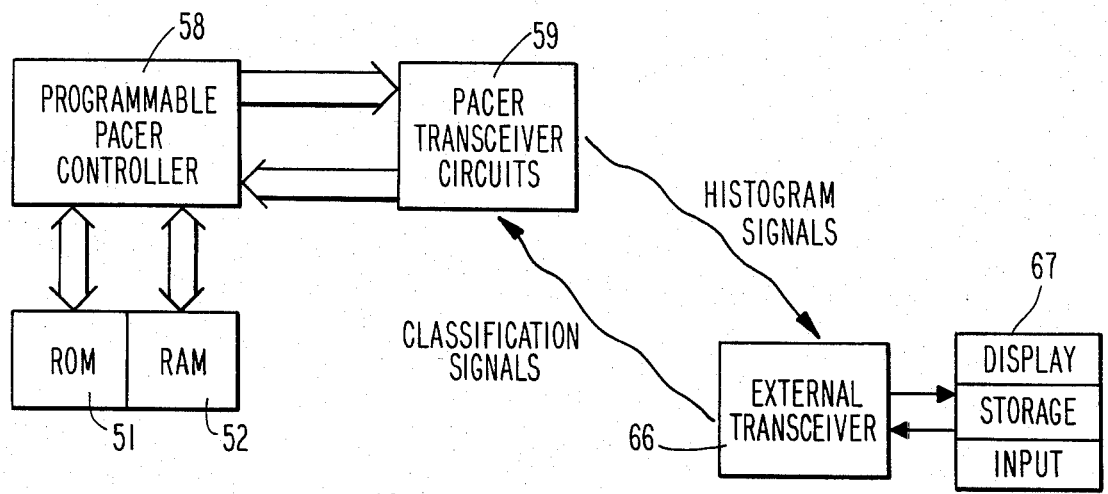
FIG. 6 is a block diagram showing two way communication between an implantable physiological device and external apparatus used to display histogram data and for inputting histogram class limits.

Referring now to FIG. 6, there is shown a block diagram of the component functional blocks of the system, for transferring information to and from the implanted device, such as a cardiac pacemaker, the system also incorporating external apparatus for purposes of such communication. The programmable pacer controller 58 is shown, in data communication with memory illustrated as ROM 51 and RAM 52. Controller 58 is in two way communication with pacer transceiver circuits which are shown as a separate block 59, which circuits may in fact be on the same chip as the controller 58, and may be considered part of the pacer circuit shown in block 61 or FIG. 1. The transceiver circuits are conventional circuits which are adapted to receive external program signals, suitably electromagnetic signals, in a manner which is conventional in present day pacemaker technology. Likewise, the circuits of block 59 are adapted to transmit data to an external device. As shown in FIG. 6, an external transceiver or programmer 66 is in two way communication with the pacer. Programmer device are known in the art, and have been described in the patent literature. The assignee has successfully utilized a Hewlett-Packard HP-85 computer for apparatus 67, which is interfaced with programmer 66. The HP-85 has a video display and is suitably combined with a ROM drawer, an I/O ROM to be placed in the ROM drawer, a 16K memory module, and a serial interface unit. A tape cartridge is used to input data and instructions to the HP-85, the HP-85 also containing a keyboard input. The video display is preferred for outputting the histograms. Software for presenting the histograms on the video display is state of the art.

With the use of the apparatus of FIG. 6, the operator is presented with a menu showing the current status of the histogram, and indicating the programming possibilities. The operator may choose to have the continuous histogram or the alternating histogram. If the alternating histogram is designated, the operator has a choice of options as to the storage cycle, e.g. one-half day, etc. The current programmed class limits are displayed on the terminal display, and the operator can change these class limits as desired. Also, the operator may instruct the programmer to read out stored histogram data, whereupon the histogram is presented on the video output in the form as set forth in FIG. 3, or it may be printed. The operator may also reset any histogram, causing the histogram data stored in memory to be set to zero. Other diagnostic information may also be called for, such as the content of various counters, including the premature beat counter, and a read out of the actual times of the occurrence of events which have been monitored, as set forth in FIG. 5C.

We claim:

1. An implantable cardiac pacemaker, having means for determining the occurrence of selected cardiac events, means for delivering stimulus pulses, and means for measuring a predetermined parameter associated with each one of said selected cardiac events, further characterized by:
    selecting means for selecting said selected cardiac events,
    registering means for registering occurrences of said selected cardiac events,
    classifying means for classifying each said registered event into respective classes of said parameter associated with said event in accordance with the measured value of said parameter,
    means for accumulating counts of said registered events for each said class, thereby providing data of the distribution of said registered events; and
    means for outputting signals representative of said accumulated counts to a location external of said implantable pacemaker.

2. The cardiac pacemaker as described in claim 1, wherein said pacemaker is a dual chamber pacemaker, and said selecting means further comprises means for selecting for registration events from the group consisting of ventricular events and atrail events.

3. The cardiac pacemaker as described in claim 1, comprising means for receiving and storing classification signals from an external source, said classifying means determining the ranges of said classes in accordance with said classification signals.

4. The cardiac pacemaker as described in claim 3, in combination with external transmitting means for enabling an operator to select and transmit said classification signals to said pacemaker.

5. The cardiac pacemaker as described in claim 1, wherein said selecting means has means for selecting pacer intervals and said classifying means has means for sorting each of said pacer intervals into one of said classes.

6. The cardiac pacemaker as described in claim 5 wherein said means for measuring comprises means for measuring the length of each said pacer interval.

7. The cardiac pacemaker as described in claim 6 wherein said selecting means further comprises means for selecting pacer intervals terminated by a sensed heartbeat.

8. The cardiac pacemaker as described in claim 6 wherein said selecting means further comprises means for selecting pacer intervals terminated by a delivered stimulus pulse.

9. The cardiac pacemaker as described in claim 1, wherein said selecting means comprises means for selecting a plurality of different types of events.

10. The cardiac pacemaker as described in claim 1, wherein said means for outputting comprises transmitting means transmitting said distribution data external of said pacemaker.

11. The cardiac pacemaker as described in claim 10, in combination with external receiving equipment for receiving said transmitted distribution data, said equipment having display means for displaying said data in histogram form.

12. A physiological device for implantation in a patient, having sensing means for sensing predetermined events in said patient, comprising:
means for recognizing said events,
means for determining the value of a given parameter associated with said events,
means for receiving classification signals from a source external to the patient,
means for defining classes of said parameter values in response to said classification signals, each said class being a predetermined range of values of said parameter,
means for determining for each of said recognized events the class of its associated parameter, first means for cummulatively storing the number of said recognized events having an associated parameter within each given one of said classes, thereby storing histogram data, and
means for outputting signals representative of said stored histogram data to an external display.

13. The device as described in claim 12, in combination with timing means for measuring a predetermined cycle length, first and second means for storing said histogram data, and switching means for alternating the cumulative storing of histogram data between said storage means every measured cycle length, said outputting means further comprising means for outputting signals representative of the stored data in each of said storage means.

14. The device as described in claim 12, comprising timing means for respectively timing out a predetermined cycle length for accumulating histogram data, and first and second storage means for storing data, and alternating means for controlling the storage of said histogram data alternately in said first and second storage means, whereby said numbers are stored in one of said storage means during a current cycle length while the other of said storage means contains numbers accumulated during the previous cycle length.

15. The device as described in claim 14, comprising select means for selecting between storing said numbers continuously in one storage means and alternating storage in different storage means each succeeding cycle length.

16. The device as described in claim 12, wherein said device comprises a microprocessor and a stored program of instructions for said microprocessor, timing means comprising said microprocessor for timing out successive time cycle lengths, second means for cumulatively storing the number of recognized events having an associated parameter within each given one of said classes, and means controlled by said timing means to alternate storage in said first and second means during successive time cycle lengths.

17. The device as described in claim 16, wherein said timing means has means to time out successive cycle lengths of a predetermined number of days said means for recognizing has means for recognizing pacer cycles, and said means for determining has means for measuring pacer interval rate.

18. The device as described in claim 16, wherein said timing means comprises a timing circuit controlled by said microprocessor which times out the length of each microprocessor program cycle corresponding to an interval between said events, and wherein said microprocessor has means for cumulatively storing said intervals until a cycle length has been determined, whereafter the next cycle length is determined.

19. The device described in claim 12, wherein said means for defining further comprises means for defining classes in terms of at least two parameters.

20. A physiological device for implantation in a patient, having sensing means for sensing means for sensing predetermined events in said patient comprising:
means for recognizing said events,
means for continuously counting cycles of time,
means for receiving classification signals from a source external to the patient,
means responsive to said classification signals for defining classes constituting ranges of time within each counted cycle,
means for cummulatively determining and storing the number of said recognized events occurring within each given one of said time classes, said numbers constituting histogram data, and
means for outputting signals representative of said histogram data.

21. The device as described in claim 20, wherein said means for continuously counting cycles of time includes means for defining a 24 hour day count cycle, and said means for defining classes defines each of said classes as a respective different period of the day.

22. The device as described in claim 20, further comprising means for storing said histogram data that has been accumulated at the time that a cycle has been counted, and means for separately storing the cumulatively determined histogram data as it is determined during the next succeeding cycle.

23. The device as described in claim 20, wherein such device is a cardiac pacemaker for delivering stimulus pulses to said patient.

24. A method of generating and utilizing histogram data, using an implanted physiological device and external apparatus, comprising:
selecting at least one of a plurality of predetermined events;
registering in said device the occurrence of said selected events;
measuring with said device a predetermined parameter associated with said events, and classifying each said parameter in said device into one of a plurality of classes of said parameter;
cummulatively counting and storing in said device the respective counts of said events having respective classified parameters; and transmitting said stored counts from said device to said external apparatus.

25. The method of claim 24, comprising generating continuous histogram data in said device.

26. The method of claim 24, comprising generating alternating histogram data in said device, and alternating said histogram data as a function of counted events.

27. The method of claim 24, comprising generating alternating histograms, and alternating said histograms as a function of elapsed time.

28. The method of claim 24, comprising the step of using said external apparatus to program said device to operate in either a continuous or alternating mode.

29. A system including an implantable pacemaker, wherein said pacemaker comprises:
selecting means for selecting at least one type of cardiac event from the group of events consisting of sensed QRS waves, sensed P waves, sensed PVC's, pacer intervals, and delivered stimuli; and histogram means for generating histogram data relating to said at least one type of cardiac unit.

30. The system as described in claim 29, wherein said selecting means comprises means for selecting any one of said group.

31. The system as described in claim 29, wherein said means for selecting comprises means for selecting at least two of said of events, and said histogram means has means for generating histogram data relating to said at least two types of events.

32. A biomedical system having an implantable device for implantation into a patient, said device characterized by
sensing means for sensing predetermined events originating with said device or said patient,
histogram means for accumulating and storing histogram data relating to at least one type of said events, and histogram control means for automatically clearing and initiating operation of said histogram means whereby it accumulates and stores said histogram data.

33. The system as described in claim 32, wherein said histogram control means further comprises timing means for timing out a predetermined time period and time control means for controlling said histogram means to accumulate said data over said period, whereby said histogram means stores said data for subsequent use after said period has been timed out.

34. The system as described in claim 32, wherein said histogram control means further comprises event counting means for counting up to a predetermined number of occurrences of said type of events and number control means for controlling said histogram means to accumulate said data for said predetermined number of occurrences, whereby said histogram means stores said data for subsequent use after the last of said occurrences.

* * * * *